(12) United States Patent
Ostrowski et al.

(10) Patent No.: US 10,209,259 B2
(45) Date of Patent: Feb. 19, 2019

(54) MICROFLUIDIC GLYCAN ANALYSIS

(71) Applicant: Agilent Technologies, Inc., Loveland, CO (US)

(72) Inventors: Magdalena Anna Ostrowski, Mountain View, CA (US); Rudolf Grimm, San Jose, CA (US); Kevin P. Killeen, Woodside, CA (US); Karla M. Robotti, Cupertino, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 167 days.

(21) Appl. No.: 14/664,709

(22) Filed: Mar. 20, 2015

(65) Prior Publication Data

US 2015/0198611 A1 Jul. 16, 2015

Related U.S. Application Data

(63) Continuation of application No. 12/362,375, filed on Jan. 29, 2009, now abandoned.

(51) Int. Cl.
*B01L 3/00* (2006.01)
*G01N 33/00* (2006.01)
(Continued)

(52) U.S. Cl.
CPC ......... *G01N 33/6842* (2013.01); *B01D 15/08* (2013.01); *B01L 3/502738* (2013.01); *B01L 3/502753* (2013.01); *F16K 99/0001* (2013.01); *G01N 27/44791* (2013.01); *G01N 30/465* (2013.01); *G01N 30/6095* (2013.01); *G01N 30/7266* (2013.01); *B01L 3/502761* (2013.01); *B01L 2200/10* (2013.01); *B01L 2300/0627* (2013.01); *B01L 2300/0874* (2013.01); *B01L 2300/0887* (2013.01); *B01L 2400/0406* (2013.01); *B01L 2400/0421* (2013.01); *B01L 2400/0487* (2013.01); *B01L 2400/0644* (2013.01); *G01N 1/405* (2013.01);
(Continued)

(58) Field of Classification Search
CPC ......... B01L 3/502707; B01L 3/502761; C12N 9/00; C12M 9/50
See application file for complete search history.

(56) References Cited

U.S. PATENT DOCUMENTS 5,291,226 A 3/1994 Schantz et al.
5,305,015 A 4/1994 Schantz et al.
(Continued)

OTHER PUBLICATIONS

Becker, E.W. et al., Fabrication of microstructures with high aspect ratios and great structural heights by synchrotron radiation lithography, galvanoforming, and plastic moulding (LIGA process), Microelectronic Engineering, 1986, pp. 35-56, vol. 4.
(Continued)

*Primary Examiner* — Nathan A Bowers

(57) ABSTRACT

Microfluidic devices and methods for analyzing glycan profiles of glycoproteins are provided. Some embodiments of the devices comprise a deglycosylation column for cleaving glycans, an optional cleaning column for removing proteins, a trapping column for enriching glycans, and a separation column for resolving glycans. The devices and methods significantly improve the speed and sensitivity of glycan analysis.

17 Claims, 14 Drawing Sheets

(51) Int. Cl.
  *G01N 33/68*   (2006.01)
  *F16K 99/00*   (2006.01)
  *G01N 27/447*  (2006.01)
  *G01N 30/46*   (2006.01)
  *G01N 30/60*   (2006.01)
  *G01N 30/72*   (2006.01)
  *B01D 15/08*   (2006.01)
  *G01N 1/40*    (2006.01)
  *G01N 30/08*   (2006.01)
  *H01J 49/00*   (2006.01)

(52) U.S. Cl.
  CPC ... *G01N 2030/085* (2013.01); *G01N 2400/00* (2013.01); *H01J 49/00* (2013.01)

(56) References Cited

U.S. PATENT DOCUMENTS

| | | |
|---|---|---|
| 6,702,256 B2 | 3/2004 | Killeen et al. |
| 2006/0171855 A1 | 8/2006 | Yin et al. |
| 2010/0003699 A1 | 1/2010 | Satomaa et al. |
| 2010/0028913 A1 | 2/2010 | Laine et al. |
| 2010/0129843 A1 | 2/2010 | Parson et al. |
| 2017/0212129 A1* | 7/2017 | Parsons .............. G01N 33/6854 |

OTHER PUBLICATIONS

Ehrfeld, W. et al., LIGA Process: Sensor Construction Techniques Via X-Ray Lithography, Tech. Digest From Solid-State Sensor and Actuator Workshop, Hilton Head, SC, 1988. IEEE.

Guckel, H. et al., Fabrication and testing of the planar magnetic micromotor, J. Micromech. Microeng., 1991, pp. 135-138, vol. 1.

Palm, Anders K. and Novotny, Milos V., A monolithic PNGase F enzyme microreactor enabling glycan mass mapping of glycoproteins by mass spectrometry, Rapid Communications in Mass Spectrometry, 2005, pp. 1730-1738, vol. 19, No. 12.

Rasmussen, James R. et al., Identification and Derivatization of (Oligosaccharyl)amines Obtained by Treatment of Asparagine-Linked Glycopeptides with N-Glycanase Enzyme, J. Am. Chem. Soc., 1992, pp. 1124-1126, vol. 114, No. 3.

Znotins, Thomas A. et al., Excimer Lasers: An Emerging Technology in Materials Processing, Laser Focus/Electro Optics, 1987, pp. 54-70, vol. 23, No. 5.

Craft, et al., "Integrated sample processing system involving on-col. protein adsorption, sample washing, and enzyme digestion for protein identification by LC-ESI MS/MS", Anal Chem. Apr. 15, 2005;77(8):2649-55.

Higel, et al., "N-glycosylation heterogeneity and the influence on structure, function and pharmacokinetics of monoclonal antibodies and Fc fusion proteins" European Journal of Pharmaceutics and Biopharmaceutics, 2016, 100: 4-100.

* cited by examiner

Table 1. Candidate glycans

| Name | Structure | Glycan Mass | Main ion species [m/z+2]+2 |
|---|---|---|---|
| G0 | 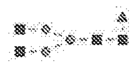 | 1462.54 | 732.27 |
| G1' G1'' |  | 1624.59 | 813.29 |
| G2 | 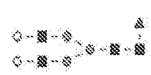 | 1786.65 | 894.32 |
| Mann-5 | 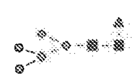 | 1234.43 | 618.21 |

Open circle: galactose

Square: GlcNAc

Closed circle: Mannose

Triangle: Fucose

*Figure 11*

MICROFLUIDIC GLYCAN ANALYSIS

BACKGROUND OF THE INVENTION

The analysis of glycoprotein structure and function, known as glycomics, has become a new and important area of research. Glycosylation is the most common post-translational modification of cell surface and extracellular matrix proteins. Glycoproteins play an important role in cell-adhesion and immune response. Changes in abundance and glycan profiles have been correlated with progression of diseases, such as cancer and rheumatoid arthritis. In addition, the analysis of glycan profiles is critical in the biotherapeutic industry. For example, antibody bio-therapeutics contain glycosylated amino acids that assist in maintaining drug activity and preventing drug rejection by the immune system. Therefore, companies that make these bio-therapeutics have to monitor and verify their glycan profiles.

Glycan analysis is usually performed by capillary electrophoresis or mass spectrometry methods. In either case, the glycans must be removed from the glycoproteins, separated and analyzed. The process of removing glycans from glycoproteins traditionally includes an in-solution enzymatic reaction with PNGase F that requires a 24-hour incubation time. After the enzyme reaction, protein precipitation is needed to separate the glycans from the proteins for analysis of the glycans. Finally, the free glycans are analyzed with mass spectrometry or capillary electrophoresis. These steps are time-consuming and cumbersome, and the manual operations are error-prone. Furthermore, a relatively large quantity of starting materials is required to generate high quality data. Therefore, a better way of performing glycan analysis is desirable.

BRIEF DESCRIPTION OF THE DRAWINGS

FIG. 11 shows glycans expected from the antibody samples analyzed in Example 1.

DESCRIPTION OF THE INVENTION

The present invention provides a new, fast, and streamlined approach to preparing, separating and analyzing glycans using a microfluidic device. Moreover, due to the design of the microfluidic device of this invention, a higher recovery yield of glycans and superior chemical separation of isoforms are achieved, and a significantly smaller amount of starting material is required, compared to traditional methods.

Prior to describing the invention in further detail, the terms used in this application are defined as follows unless otherwise indicated.

Definition

In this specification and the appended claims, the singular form "a," "an," and "the" include plural reference unless the context clearly dictates otherwise.

A "microfluidic device" is a device comprising chambers and/or channels of micron or submicron dimensions that allow passage of fluid. The chambers or channels are generally 1 µm to less than 1000 µm in diameter (or, if not circular, the largest dimension of the cross section), such as 1 µm to 500 µm, 10 µm to 300 µm, 50 µm to 250 µm, by way of examples.

A "column" is an apparatus for a particular purpose, usually for preferentially binding or retaining a substance or class of substances. Typically, a column comprises a housing in which a filling is located, and the filling is capable of preferentially binding or retaining a substance or class of substances. In some embodiments, the filling may merely provide a medium for various substances to move through, while the substances move in different speeds (e.g., due to an electric field). A column (or a housing or filling) can be of any size, shape or structure, and made of any material, that is consistent with the purpose of the column.

As used herein, "connect" may occur by direct or indirect connections. A direct connection means two objects that are connected have a physical contact with each other. An indirect connection means two objects that are connected do not physically contact each other, but are connected through at least one object in between.

As used herein, if two objects are in "fluid communication," there is a conduit between the two objects that allows fluid to flow from one of the objects to the other. A conduit may be a pore, orifice, opening, channel, tube, or the like.

The term "carbohydrate" refers to any compound in the carbohydrate family, including sugars, disaccharides, oligosaccharides, polysaccharides, simple carbohydrates, complex carbohydrates, and the like.

Device and Methods

Figure 1A:
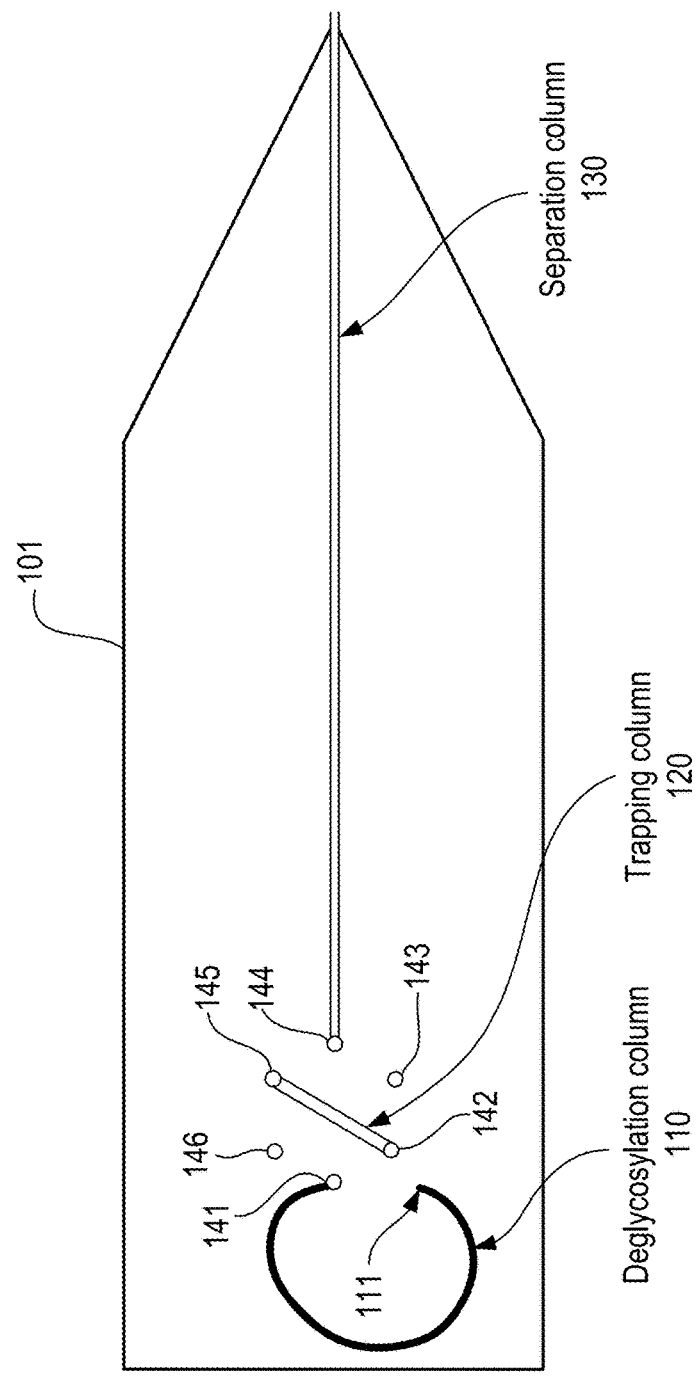
FIG. 1A is a schematic diagram of a top-down view of a microfluidic chip that can be used for glycan analysis of glycoproteins.

FIG. 1A illustrates an exemplary device 101 in accordance with one embodiment of the present invention. The device 101 comprises a deglycosylation column 110 for cleaving glycans from glycoprotein samples, a trapping column 120 for trapping and enriching the cleaved glycans, and a separation column 130 for separating the glycans. Although a particular shape is drawn for the device 101 and each component of the device, other variations in shape or relative size can be used for this invention. Similarly, the other devices and components described in this disclosure are not limited to the shapes or sizes shown in the drawings.

The deglycosylation column 110 comprises a solid support to which an enzyme is attached, with the enzyme capable of cleaving carbohydrates from a glycoprotein. In most glycoproteins, the carbohydrate moiety is attached to the nitrogen of the amide group in asparagine residues (N-linked glycans), or the oxygen of the hydroxyl group in serine or threonine residues (O-linked glycans). Any enzyme that can cleave the carbohydrate moiety from glycoproteins can be used in the present invention, including enzymes that are specific for N-linked or O-linked glycans. These enzymes are known in the art and include, without being limited to, PNGase F, β-N-Acetyl-glucosaminidase, α-Fucosidase, β-Galactosidase, α-Galactosidase, α-Neuraminidase, α-Mannosidase, β-Glucosidase, β-Xylosidase, β-Mannosidase, Endo $F_1$, Endo $F_2$, Endo $F_3$, and Endo H. Materials and methods of immobilizing proteins to solid supports are also known in the art (see, e.g., Palm and Novotny, 2005). For example, the solid support in the deglycosylation column 110 may be glass or polymer beads, or a monolithic medium (such as polymethacrylate, polystyrene, polyacrylamide, or the like).

The trapping column 120 is capable of preferentially binding carbohydrates but not proteins. For example, hydrophilic interaction liquid chromatography (HILIC) stationary phase can be used to retain and desalt the glycans released from glycoproteins in the deglycosylation column. The separation column 130 is capable of separating glycans based on their physical and/or chemical properties. Two main categories of the separation column are liquid chromatography columns and capillary electrophoresis columns.

Figure 1B:
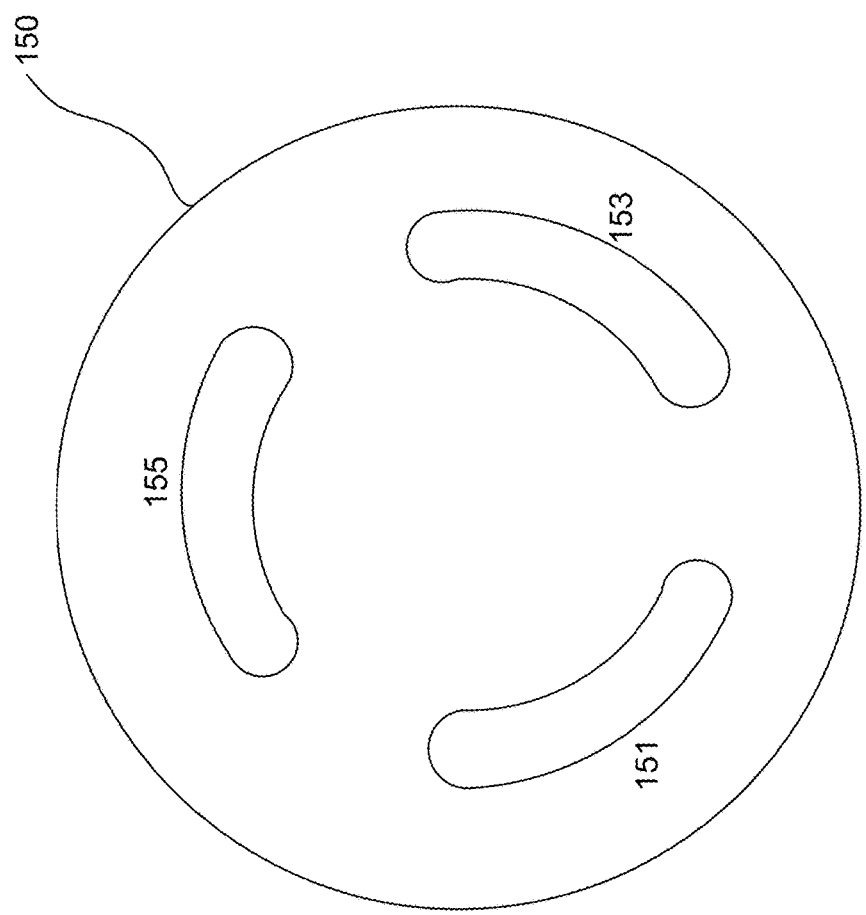
FIG. 1B is a schematic diagram of a top-down view of a switching element in the form of a rotor that can be coupled with the chip shown in FIG. 1A.
Figure 1C:
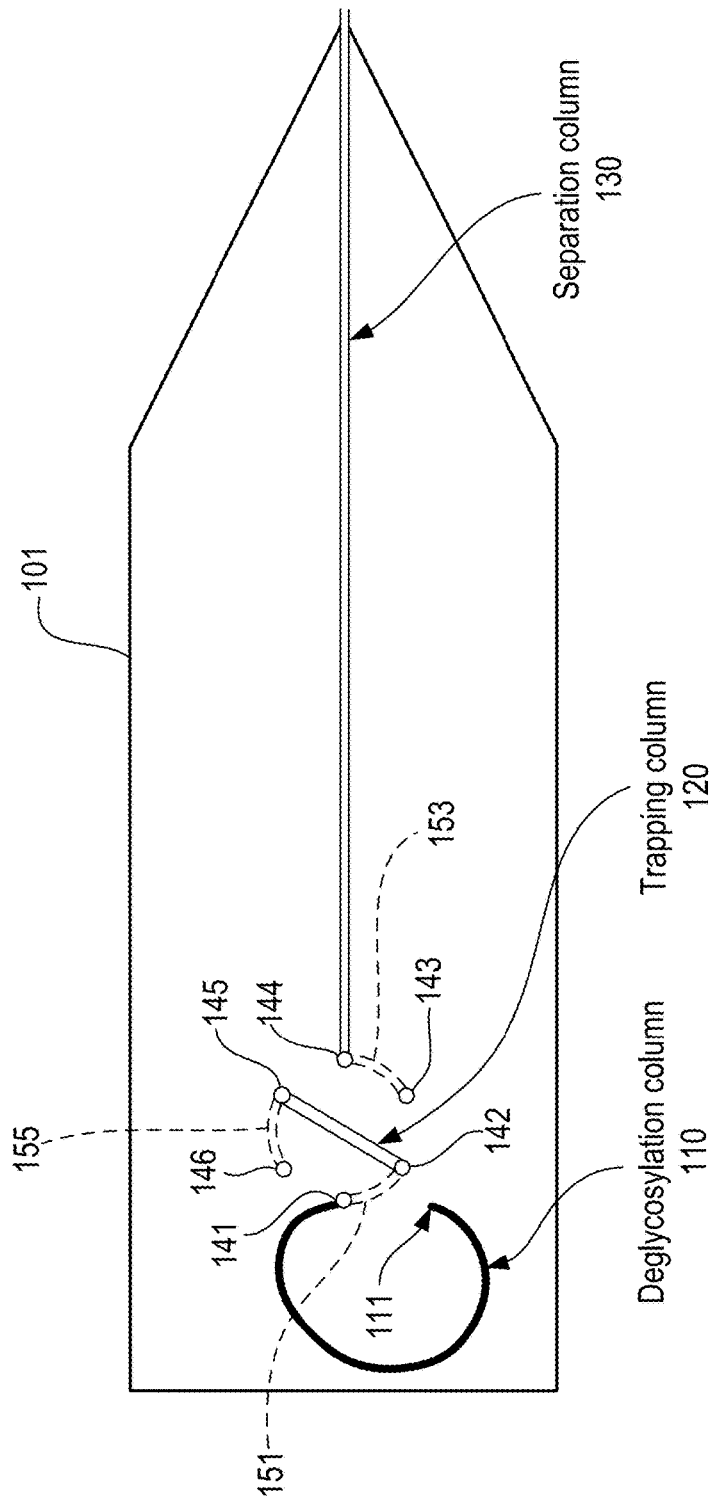
FIG. 1C shows one state of a valve system formed when the chip of FIG. 1A is coupled with the rotor of FIG. 1B. In this state, the trapping column is connected to the deglycosylation column.

The device 101 also contains a plurality of inlet/outlet ports 141-146. An inlet/outlet port (or "port") can be a hole, orifice, opening, any of the above connected to a conduit (especially a short conduit), or the like, as long as the port allows fluid to pass from one end of the port to the other. The ports 141-146 can be used to connect different parts of the device at different stages when device 101 is aligned with and coupled to appropriate channels. For example, device 101 can be fit on top of a rotor 150 that comprises three channels 151, 153 and 155 (FIG. 1B). The rotor 150 can be rotated so that different ports in device 101 are connected by each channel in the rotor when the rotor is in a different position. For example, the rotor can be rotated to a position wherein inlet/outlet ports 141 and 142 are connected by channel 151 (FIG. 1C). At this position, inlet/outlet ports 143 and 144 are also connected (by channel 153), and so are inlet/outlet ports 145 and 146 (by channel 155). A sample that contains, or is suspected to contain, glycoproteins is loaded into the deglycosylation column 110 through an inlet port 111. The glycoproteins are digested in the deglycosylation column 110, releasing free glycans as well as the remaining part of the glycoproteins. This mixture flows to the end of the deglycosylation column, which is connected to port 141, and enters the trapping column 120 via channel 151. In the trapping column 120, the glycans are bound to the carbohydrate-binding substance, while the remaining components of the mixture flow through the column and are collected or discarded via channel 155.

Figure 1D:
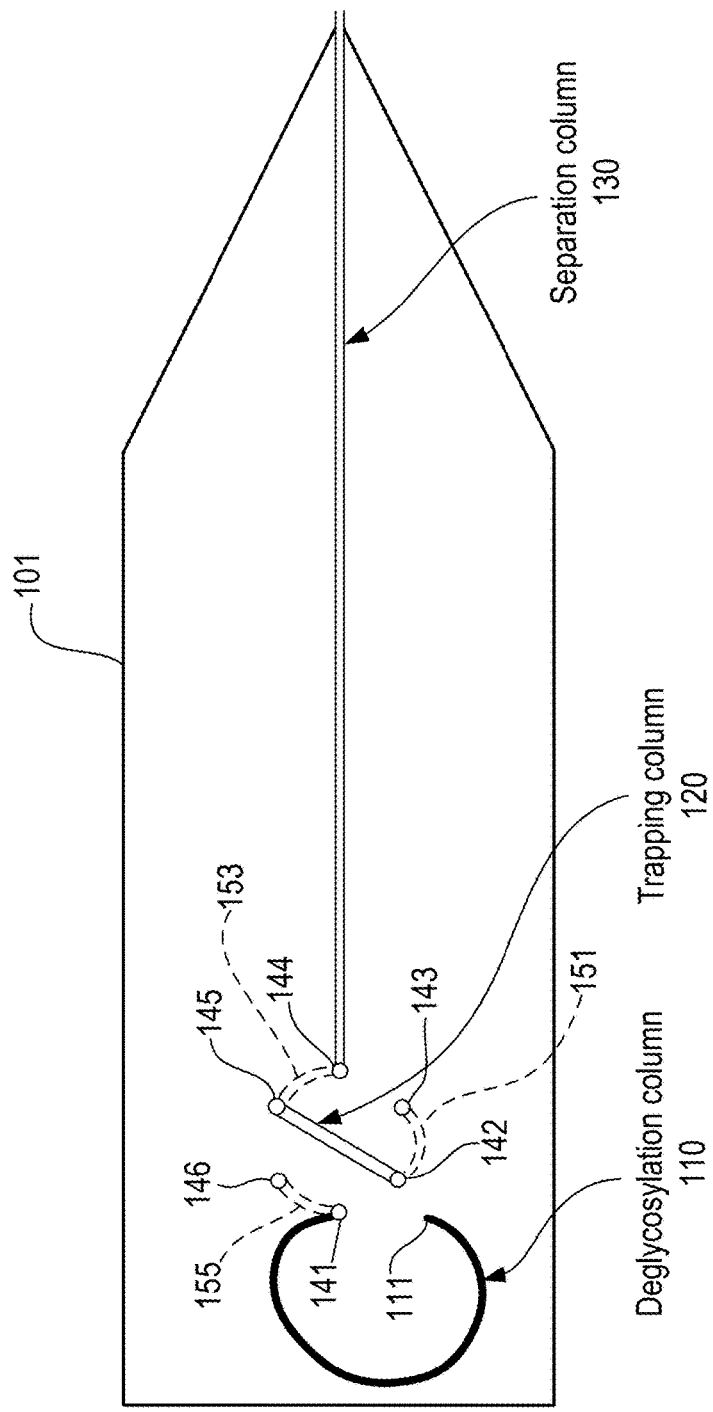
FIG. 1D shows another state of the valve system in which the trapping column is connected to the separation column.

The system is then switched to a different position (see FIG. 1D), in which the following inlets/outlets are connected: port 142 with port 143, port 144 with port 145, and port 146 with port 141. Thus, the trapping column 120 and the separation column 130 are now in fluid communication through channel 153, and the deglycosylation column 110 is no longer connected with the trapping column 120. An elution solution can be added to the trapping column 120 from port 143, and the eluate flows from port 145 to port 144 and enters the separation column 130. The glycans are then separated in the separation column 130. The outlet of the separation column 130 can be connected to the sample inlet of a mass spectrometer to further analyze the glycans by mass spectrometry.

Although a rotor is described above as a switching element to change the fluid communication state of the columns in device 101, other switching elements can be utilized. For instance, a set of channels and valves can be engaged with device 101 so that, upon switching one valve or multiple valves, the deglycosylation column is disconnected from the trapping column, and the trapping column is connected with the separation column.

In some embodiments, the deglycosylation column 110 and the trapping column 120 are continuous. For example, instead of two discontinuous columns 110 and 120, device 101 can have a chamber that comprise a deglycosylation material (a deglycosylation enzyme immobilized to a solid support) in a first part of the chamber to constitute a deglycosylation column, and a trapping material (which preferentially binds carbohydrates but not proteins) in the next part of the chamber to form a trapping column. As another example, a deglycosylation column can be connected with a trapping column by an orifice or conduit in device 101, so the two columns are in fluid communication within the structure of device 101. For these embodiments, a simpler switching element can be used, which does not have to connect the deglycosylation column with the trapping column. It is conceivable that the switching element may comprise a minimum of a channel and a valve controlling the channel, wherein the channel can be positioned to connect the trapping column and the separation column. When the valve is switched off, the trapping column is not in fluid communication with the separation column. In this state, sample loading, deglycosylation, and glycan enrichment (trapping) can be performed. The valve is then switched on to allow fluid communication between the trapping column and the separation column for eluting the trapping column and separating the glycans.

Figure 2:
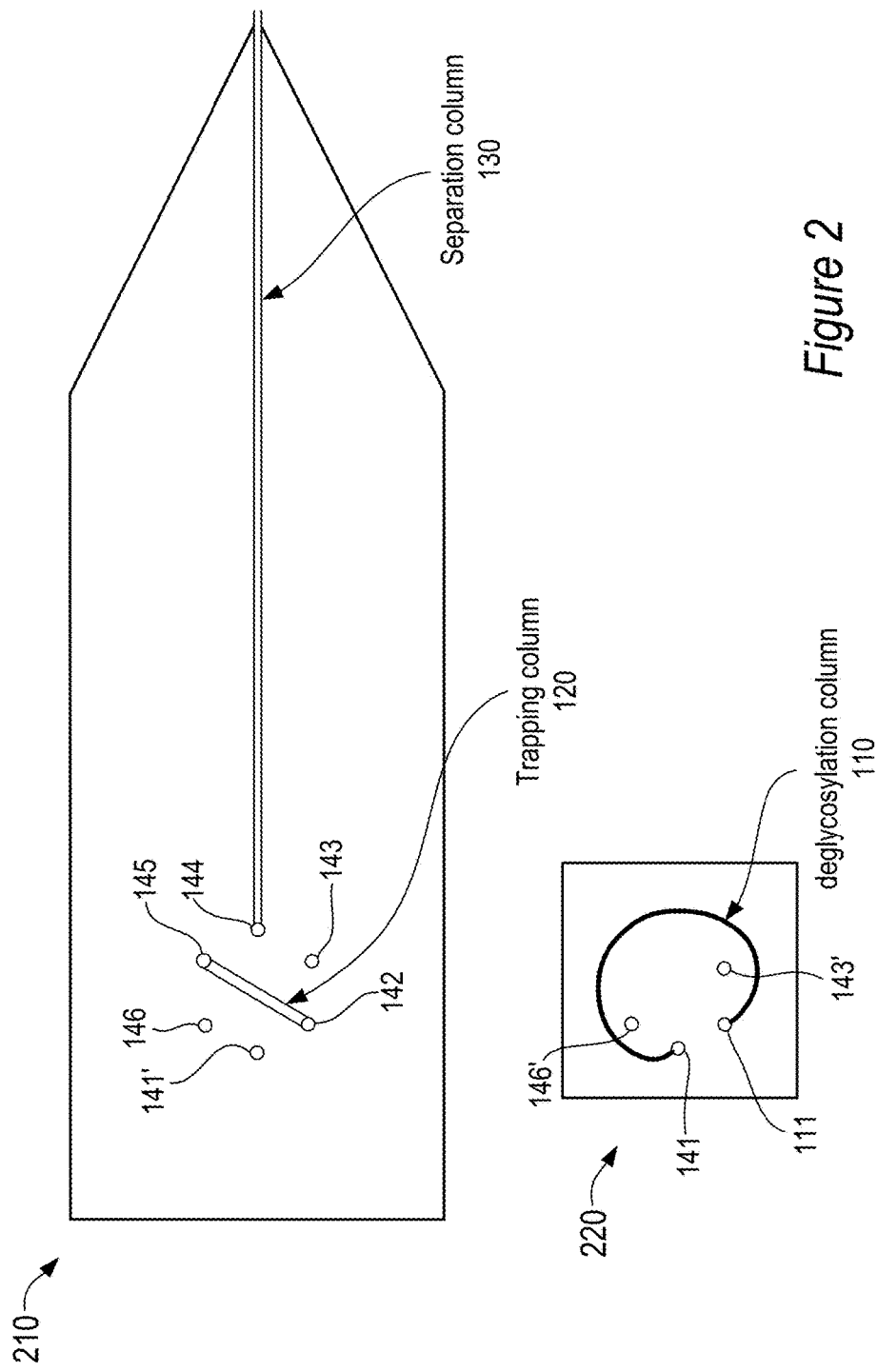
FIG. 2 shows two layers of a microfluidic chip.

In some embodiments, different parts of the device are located on different layers or chips, which are assembled to form the device (see, e.g., U.S. Patent Publication No. 2006/0171855). For example, FIG. 2 shows a chip 210 containing the trapping column 120 and the separation column 130. Another chip ("deglycosylation chip") 220 contains the deglycosylation column. The deglycosylation chip 220 can be connected to the chip 210 by, for example, mechanically sealing on top of chip 210, in a manner that allows fluidic communication between inlet/outlet port 141 of chip 210 with port 141' of deglycosylation chip 220. Note that the deglycosylation chip 220 does not contain counterparts of inlet/outlet ports 144 and 145 in this design, because 144 and 145 are used for communication between the trapping column and the separation column, both of which are on chip 210. Chip 220, however, may have counterparts of inlet ports 143 and 146 (143' and 146') for alignment purposes only. Thus, port 143 is aligned with port 143', and port 146 is aligned with port 146' when chips 210 and 220 are assembled.

In operation, the assembled, two-chip device is engaged with a switching element that contains multiple channels, such as the rotor shown in FIG. 1B. A sample is loaded into inlet port 111, which is the inlet to the deglycosylation column 110. The reaction mixture after deglycosylation flows, sequentially, to inlet/outlet port 141, inlet/outlet port 141' on chip 210 which is connected to port 141, a channel in the rotor that connects port 141' with port 142, port 142, and trapping column 120. After trapping, the rotor is switched to allow fluid communication between trapping column 120 and the separation column 130 (through a channel in the rotor that connects port 144 and port 145), and the glycans are eluted and separated as described above.

Figure 3:
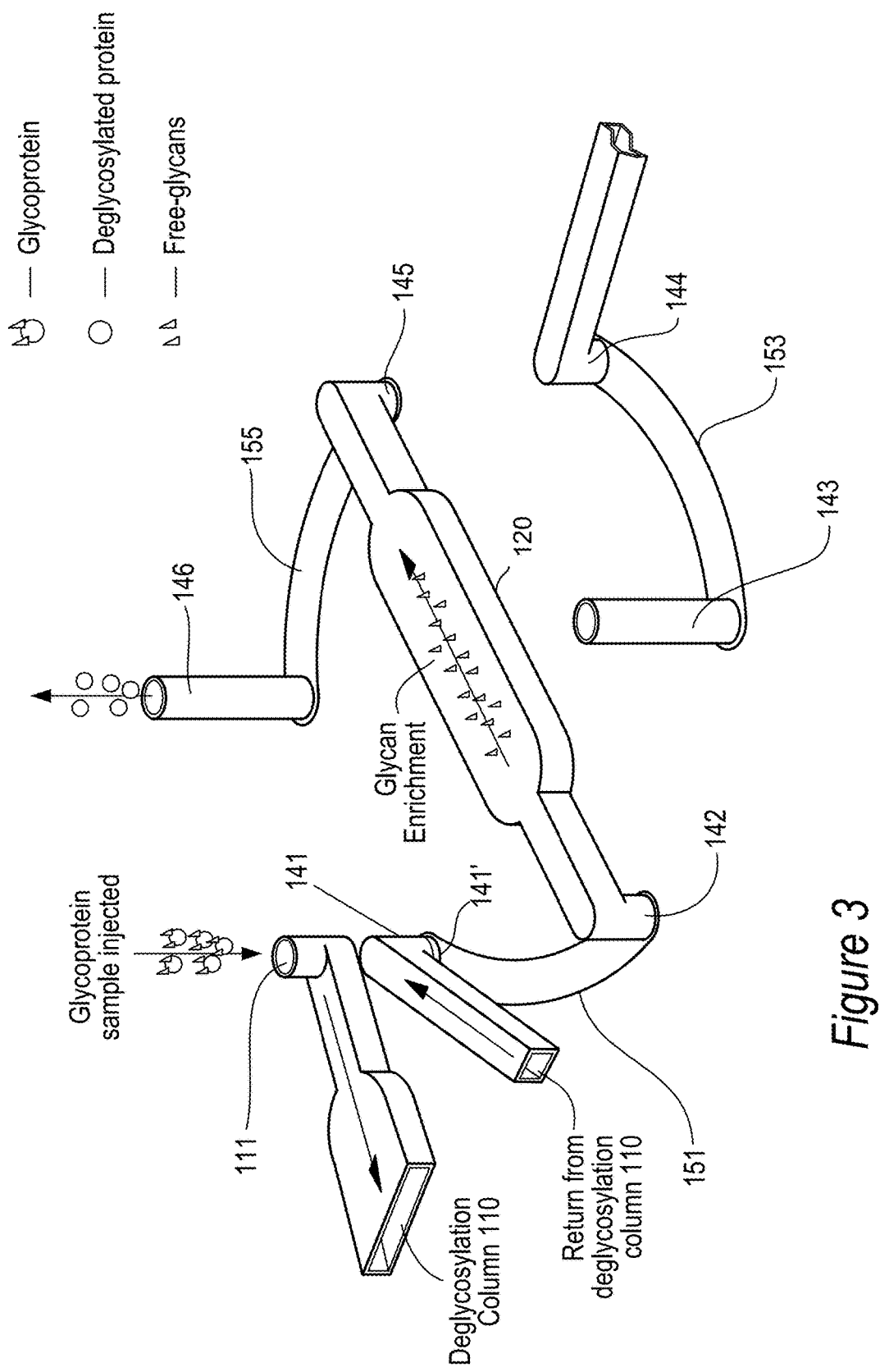
FIG. 3 shows a three-dimensional view of how deglycosylation and glycan enrichment occur in a microfluidic device of the present application. Some channels from a switching element, which is coupled with the device, are also shown.
Figure 4:
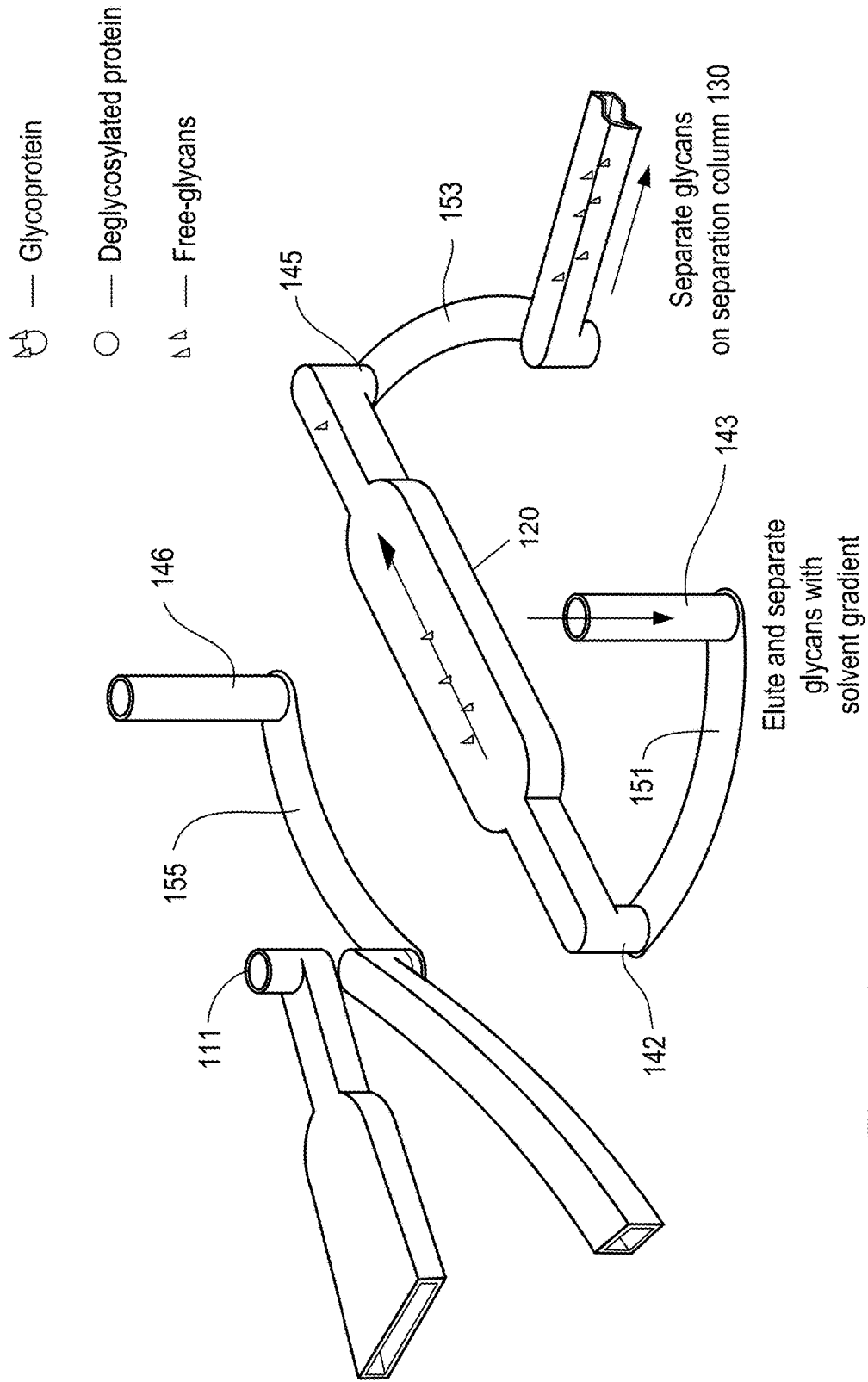
FIG. 4 shows a three-dimensional view of a microfluidic device switched to a position to send collected glycans to a separation column. Some channels from a switching element, which is coupled with the device, are also shown.

FIGS. 3 and 4 show three-dimensional views of how some embodiments of two-layer devices work in conjunction with a switching element. As illustrated in FIG. 3, the sample is injected into inlet port 111 to enter the deglycosylation column, which is in the shape of a loop in the embodiment in this figure. Only the beginning part and the ending part of the loop are shown. This particular embodiment differs from the one shown in FIG. 2 in that port 141 is below inlet port 111, which is a variation that serves the same function. The output from the deglycosylation column is led into the trapping column through channel 151, and glycan enrichment occurs in the trapping column, which is in a lower layer compared to the deglycosylation column. Proteins without a carbohydrate moiety flow through the trapping column and exit through channel 155. In FIG. 4, the trapping column is connected with channels 151 and 153 (by switching a switching element not completely shown in the figure), an elution solution is applied to the trapping column through channel 151, and glycans are eluted from the trapping column and enters the separation column through channel 153.

In some embodiments, the device further comprises a cleaning column that is capable of preferentially binding proteins but not carbohydrates. For example, the C18, C8, or other reverse phase material retains protein while passing free glycans. For proteins such as antibodies, protein A can be used to bind the antibody but not the glycans. The proteins bound to the cleaning column can be discarded or analyzed to understand the protein profile and content in the sample. These embodiments have inlet/outlet ports that, when coupled with a switching element, allow for connection between the deglycosylation column and the cleaning column, and between the cleaning column and the trapping column, either at the same time or not. It is also contemplated that in some embodiments, the deglycosylation column can be connected with the trapping column, and the trapping column with the cleaning column, either at the same time or not. Thus, in some embodiments, all of these three columns can be connected at the same time in the order of deglycosylation-cleaning-trapping, or deglycosylation-trapping-cleaning.

Figure 5:
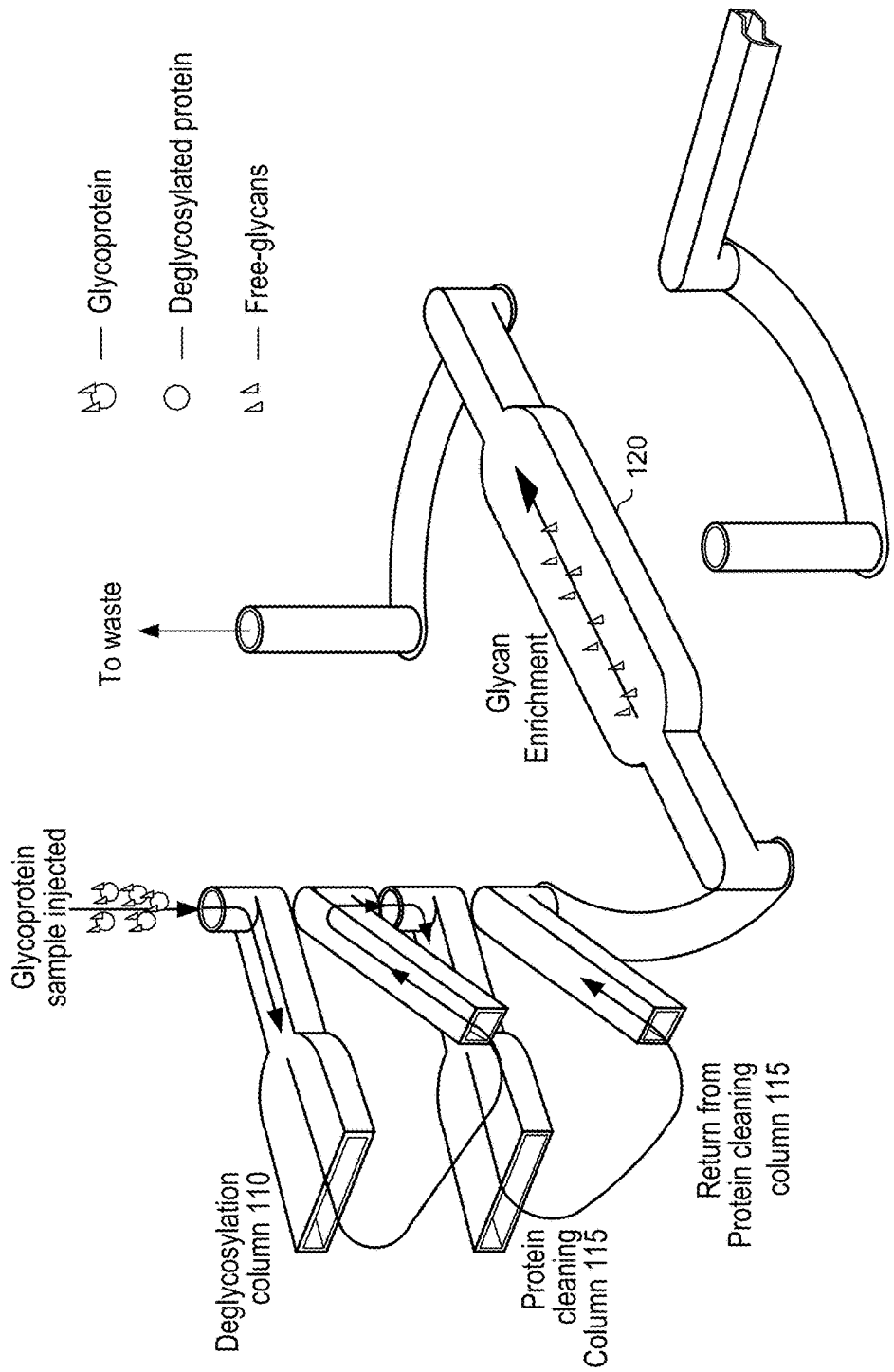
FIGS. 5 and 6 illustrate a three-dimensional view of a microfluidic device that comprises three layers. Some channels from a switching element, which is coupled with the device, are also shown.
Figure 6:
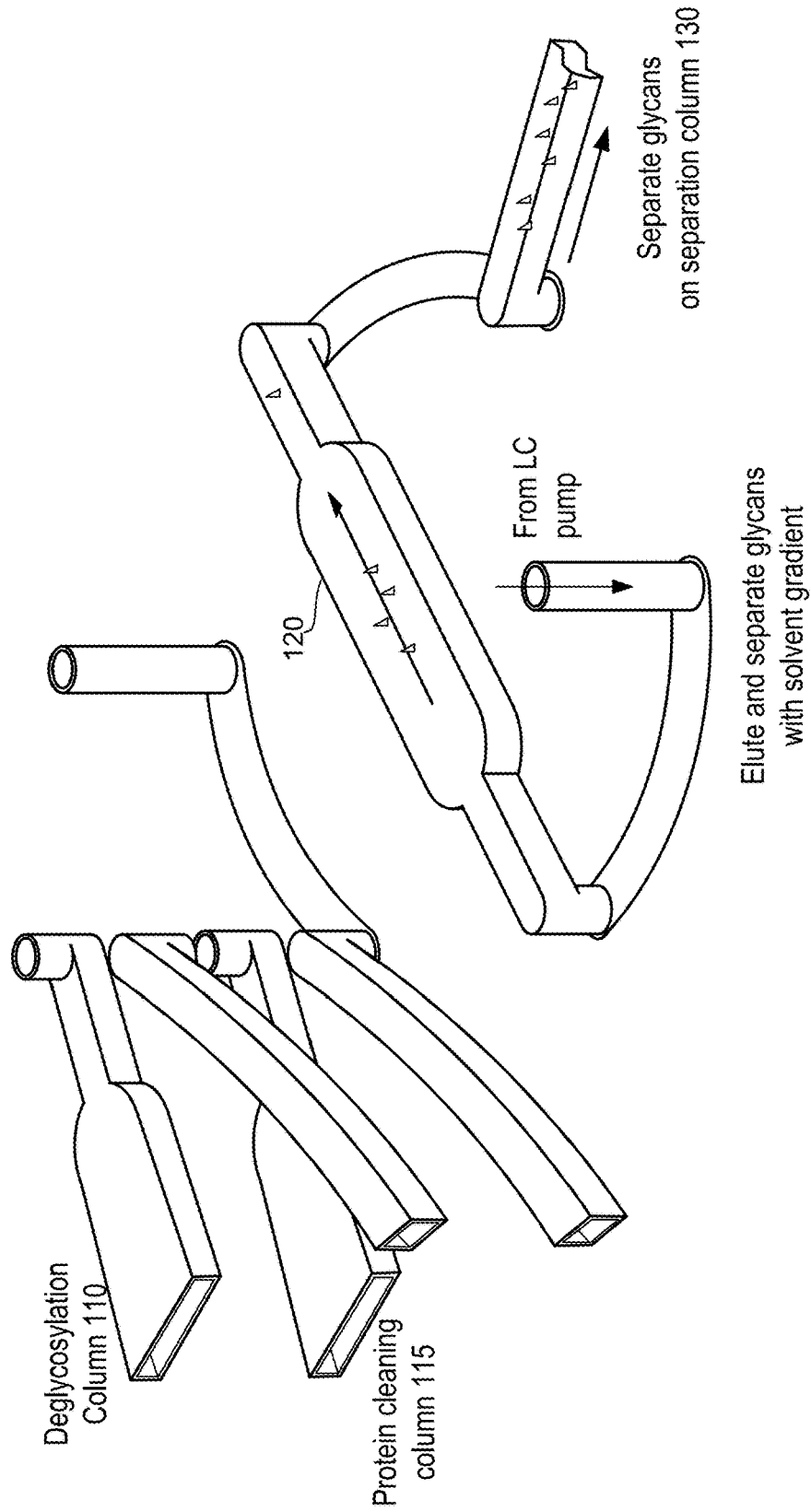

FIGS. 5 and 6 illustrate a three-dimensional view of a device that comprises a cleaning column in a three-layer design. The first layer includes a deglycosylation column 110, a protein cleaning column 115 is in the middle layer, and the bottom layer contains a trapping column 120 and a separation column 130. The figures also show three channels from a switching element.

Example 1 describes experiments in which the embodiment depicted in FIGS. 5 and 6 was used to analyze glycan compositions in an antibody sample. The results demonstrate that the device of the present invention enables a fast analysis, and it is possible to preserve the original chemical structures of the glycans in the fast analysis. In contrast, a traditional in-solution analysis performed in parallel indicates that chemical structures of the glycans changed during the prolonged incubation of the traditional analysis. Unexpectedly, isoforms of the glycans, now in their original structures (amino glycan forms), can be resolved much more readily in the separation column, whereas it had been necessary to employ a long and more time-consuming and thus expensive separation process to separate the isoforms, a problem that had been troublesome in the field.

The speed of the present methods depends on complexity of the samples, as longer separation is required when more glycans need to be separated. In addition, if finer separation is desired, such as separation of isomers, a longer separation column and thus longer separation time is needed as well. By the present methods, the process of deglycosylation, cleaning, trapping and separation can generally be achieved in one minute to an hour, such as in 1, 2, 3, 4, 5, 10, 15, 20, 25, 30, 35, 40, 45, 50, 55, or 60 minutes. In some embodiments, the process is performed under conditions that allow a substantial amount of the glycans to remain in amino glycan forms. This substantial amount may be, for example, at least 95, 90, 80, 70, 60, 50, 40, or 30% of the glycans in the sample.

The results also indicate that a small amount of sample (100 ng glycoproteins) yielded strong signals, suggesting that the amount of the sample can be reduced. Thus, in some embodiments, the present methods can be used to analyze a sample containing up to 10, 20, 30, 40, 50, 60, 70, 80, 90 or 100 ng of glycoproteins.

Thus, some embodiments of the present invention provide devices, usually in the form of chips, that comprise:

a deglycosylation column comprising a solid support and an enzyme immobilized to the solid support, wherein the enzyme is capable of cleaving carbohydrates from glycoproteins;

a trapping column capable of binding carbohydrate;

a separation column capable of separating carbohydrates; and a plurality of inlet/outlet ports;

wherein said ports are configured so that when said device is aligned with a switching element that comprises a channel or a plurality of channels, the combination of said ports, columns and channel(s) forms a valve system that can be switched between at least a first state and a second state, the first state allowing fluid communication between the deglycosylation column and the trapping column, and the second state allowing fluid communication between the trapping column and the separation column.

The device can optionally further comprise a cleaning column that is capable of binding proteins. The cleaning column may be used to bind and discard proteins, which are undesirable in glycan analyses. Alternatively, the cleaning column can be used to collect proteins for a protein analysis in addition to the glycan analysis.

In some other embodiments, the device may comprise a deglycosylation column, a cleaning column, and a separation column, without the trapping column. These embodiments fall into two groups. One group can be used for protein analyses, in which case the separation column is one for separation of proteins rather than carbohydrates. A switching element capable of connecting the cleaning column with the separation column is to be used in conjunction with this group. The other group can be used for a shortened glycan analysis process, in which glycan enrichment is omitted. Embodiments in this group comprise a separation column for separating carbohydrates.

Microfluidic devices are typically fabricated by generating channels and chambers in a material that forms the device or layers of the device. Suitable materials for forming the device, or layers of the device, are selected with regard to physical and chemical characteristics that are desirable for proper functioning of the microfluidic device. For example, a device is fabricated from a material that enables formation of high definition features, i.e., microchannels, microchambers and the like, that are of micron or submicron dimensions. Thus, the material must be capable of microfabrication using, e.g., dry etching, wet etching, laser etching, laser ablation, molding, embossing, or the like, so as to have desired miniaturized surface features. Microstructures can also be formed on the surface of a material by adding material thereto, for example, polymer channels can be formed on the surface of a glass substrate using photo-imageable polyimide. Also, all device materials used should be chemically inert and physically stable with respect to any substance with which they comes into contact when used to introduce a fluid sample (e.g., with respect to pH, electric fields, etc.). Suitable materials for forming the present devices include, but are not limited to, polymeric materials, ceramics (including aluminum oxide and the like), glass, metals, composites, and laminates thereof.

Polymeric materials are typically organic polymers that are homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene) (ABS), acrylate and acrylic acid polymers such as polymethyl methacrylate, and other substituted and unsubstituted polyolefins, and copolymers thereof. Polyimide is of particular interest and has proven to be a highly desirable substrate material in a number of contexts. Polyetheretherketones (PEEK) also exhibit desirable biofouling resistant properties.

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite materials include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, that has been co-extruded with a second, thin layer of a thermal adhesive form of polyimide known as KJ®, both available from DuPont (Wilmington, Del.).

The present devices can be fabricated using any convenient method, including, but not limited to, micromolding and casting techniques, embossing methods, surface micromachining and bulk-micromachining. The latter technique involves formation of microstructures by etching directly into a bulk material, typically using wet chemical etching or reactive ion etching ("RIE"). Surface micro-machining involves fabrication from films deposited on the surface of a substrate. An exemplary surface micro-machining process is known as "LIGA." See, for example, Becker et al. (1986), Ehrfeld et al. (1988), and Guckel et al. (1991). LIGA involves deposition of a relatively thick layer of an X-ray resist on a substrate followed by exposure to high-energy X-ray radiation through an X-ray mask, and removal of the irradiated resist portions using a chemical developer.

Another technique for preparing the present devices is laser ablation. In laser ablation, short pulses of intense ultraviolet light are absorbed in a thin surface layer of material. Preferred pulse energies are greater than about 100 millijoules per square centimeter and pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation will typically involve use of a high-energy photon laser such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987), and in U.S. Pat. Nos. 5,291,226 and 5,305,015 to Schantz et al.

Another aspect of this invention provides systems that comprise a device of the present invention. The system may further comprise a switching element for switching a valve system to allow selective connections between the various columns of the device. The switching element may be, for example, a rotor comprising a plurality of channels that can be aligned with the inlets/outlet ports of the chip when the chip is engaged with the rotor. Furthermore, the rotor can be switched between at least two different states, each of which allows for connection of different ports in the chip. The switching element may also be a sliding element that can be slid between at least two different positions to connect different ports, such as those described in U.S. Pat. No. 6,702,256. Other switching mechanisms can also be used. The system may optionally comprise an interface for transmitting the output of the device (separated glycans) to the inlet of a mass spectrometer or other analysis tools. Alternatively, the output of the device may directly enter the ionization area of a mass spectrometer. The system may further comprise a mass spectrometer or other analysis tools.

Other embodiments also provide kits that comprise a device of the present invention. The kit can further comprise any one or any combination of the following: sample solution, elution solution for any of the columns, reconstitution reagents for any of the columns, a standard sample (such as an antibody standard, glycan standard, etc.), instructions for use, and a container for the components.

The following examples are offered to illustrate various embodiments of this invention and are not to be construed in any way as limiting the scope of the present invention. While certain embodiments of this invention are particularly shown and described, various changes in form and details may be made therein without departing from the spirit and scope of the invention.

EXAMPLES

In the examples below, the following abbreviations have the following meanings. Abbreviations not defined have their generally accepted meanings.

° C.=degree Celsius
hr=hour
min=minute
sec=second
mM=millimolar

μM=micromolar
nM=nanomolar
μm=micrometer
ml=milliliter
μl=microliter
nl=nanoliter
mg=milligram
μg=microgram
HPLC=high performance liquid chromatography
LC=liquid chromatography
MS=mass spectrometry
QTOF=quadrupole-time of flight Example 1

Glycan Analysis with On-Chip Enzymatic Reactions

Chip Fabrication

PNGase F enzyme was chemically attached to epoxide-modified 5 μm silica beads in phosphate buffer (pH 8) over 22 hr. The beads were then packed into a chamber located in a first polyimide chip. Reverse-phase 5-μm C8 beads were packed into a second chamber on a second polyimide chip for protein cleaning. The third chip layer contained a sample enrichment column (40 nl), a separation column (75 mm) filled with graphitized carbon for HPLC analysis, and an integrated MS tip for input into a mass spectrometer. All three chips were stacked, aligned and inserted into a chip frame holder.

Methods

The antibody samples were diluted in phosphate buffer to a concentration of 6 pmol/μl in phosphate buffer (pH 7.5). The HPLC system operated using typical mobile phases of 0.1% formic acid in MS-grade water (Solvent A) and 0.1% formic acid in acetonitrile (Solvent B). The autosampler was set to inject 0.1 μl of antibody. The capillary pump was set to pass the sample through the deglycosylation column and the C8 column at a flow rate of 1 μl/min. This flow rate corresponds to a deglycosylation time of 8 seconds, and resulted in 100% deglycosylation. The solvent used for loading and deglycosylation was 50 mM sodium phosphate. The gradient for fast deglycosylation and glycan analysis was 2-32% Solvent B in 1.5 min, 32-75% Solvent B in 30 sec and held at 75% Solvent B for another 30 sec, followed by 75-2% Solvent B over the last 30 sec. with a nano pump flow of 300 nl/min. A longer gradient was used to separate isomers.

The separated glycans were analyzed using a QTOF tandem mass spectrometer with an electrospray ionization source. The mass spectra were recorded in positive ion mode. Voltage of the cap was set to 1750V, with a drying gas of 325° C. at 8 L/min. The fragmentation voltage was 120V. The skimmer voltage was 65V. Data was acquired in 2 GHz mode.

Results

Antibody samples were deglycosylated and the resulting glycans were separated by HPLC and analyzed by mass spectrometry, using the chip and method as described above.

Figure 7:
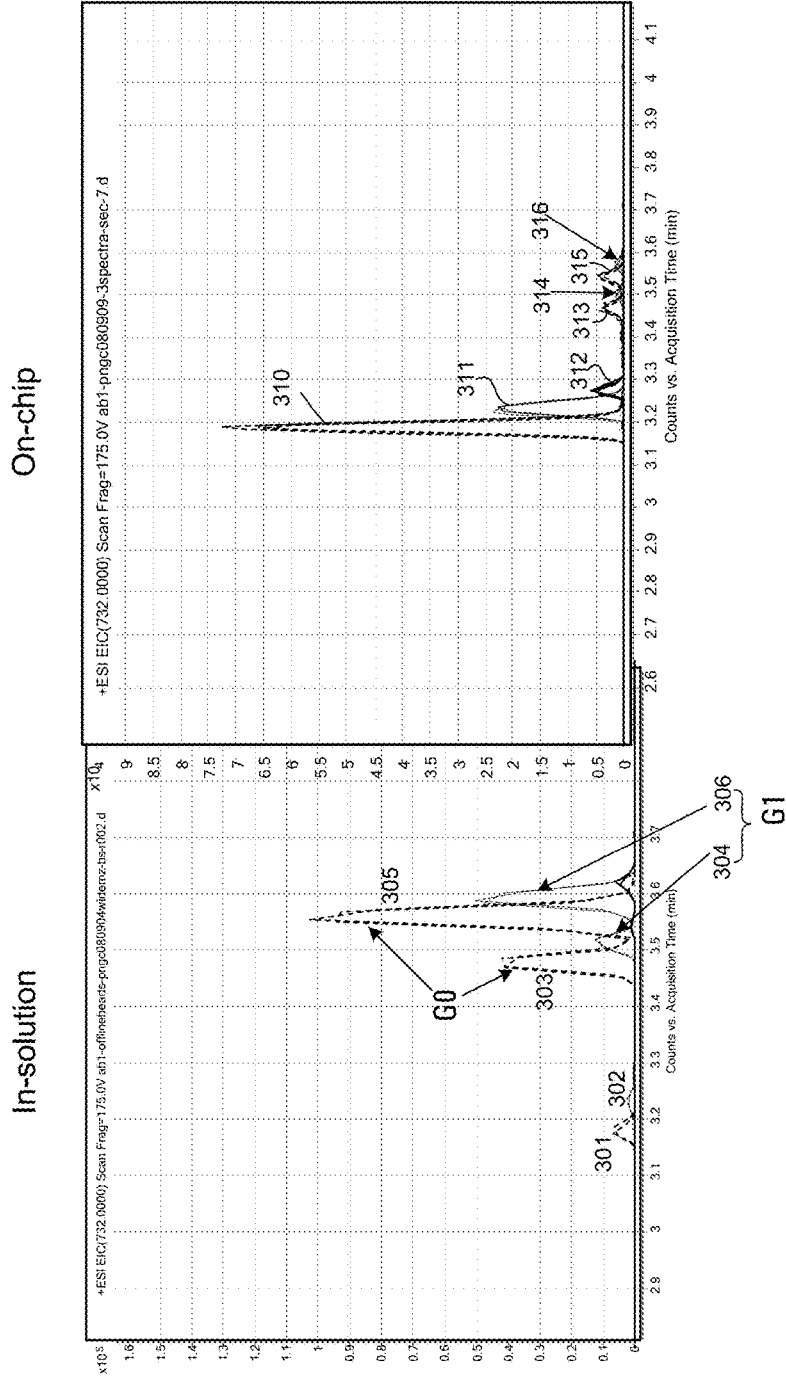
FIG. 7 shows the mass spectral scan of an antibody sample that has been processed on-chip (right-hand side) or in-solution (left-hand side).

FIG. 7 (left-hand side) shows a typical result from the traditional, in-solution analysis in which the sample was cleaved by PNGase F in solution overnight in a protocol that lasted 24 hours in total. Of the major peaks, 303 and 305 correspond to two stereoisomers (α- and β-anomers) of G0, and 304 and 306 correspond to the two isomers of G1, G1' and G1" (see FIG. 11). All these glycan species eluted around 3.4-3.7 minutes. In addition, there are also minor peaks 301 and 302 eluting around 3.2 minutes. However, the results of the on-chip analysis using the same sample were different. As shown in FIG. 7, right-hand side, the sample yielded a prominent peak (310) and two smaller peaks (311 and 312), all around 3.2 minutes. Four minor peaks 313-316 appeared between 3.4 and 3.7 minutes, where the major peaks in the in-solution analysis were. In fact, the positions of 313-316 were in good agreement with peaks 303-306 in the in-solution analysis, just like peaks 310 and 311 eluted at about the same times as peaks 301 and 302.

Figure 8:
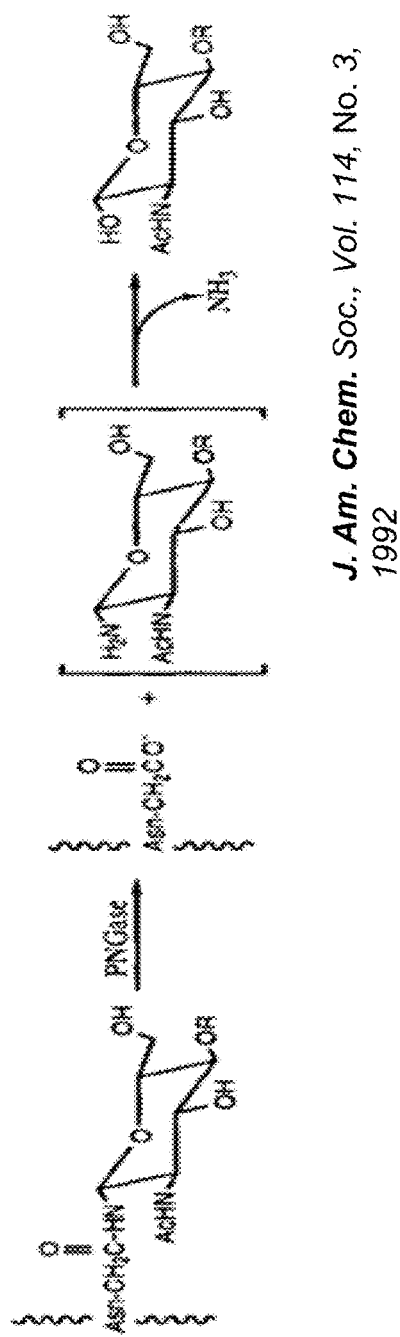
FIG. 8 shows the chemical mechanism of enzymatic action of PNGase F.
Figure 9:
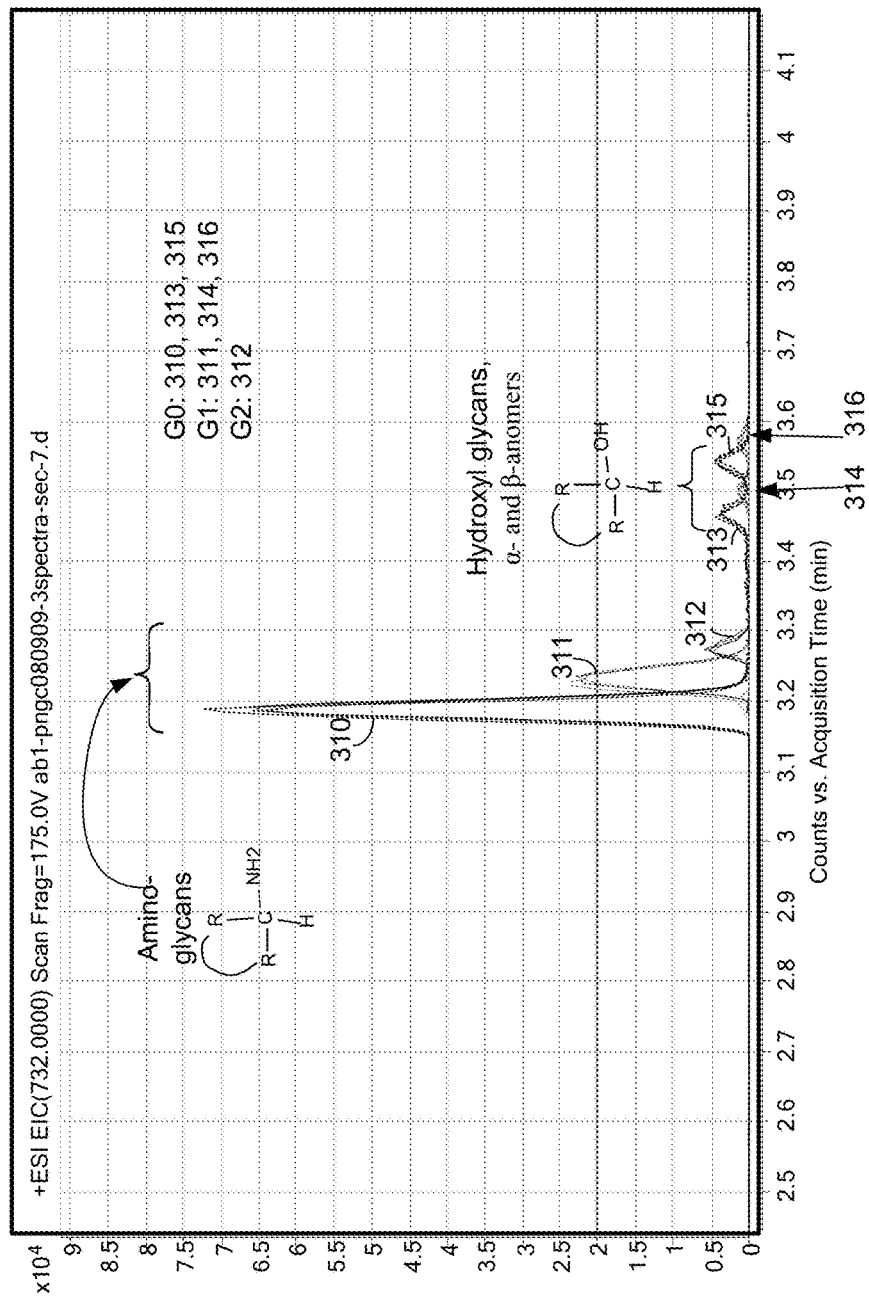
FIG. 9 shows the identity of the glycans corresponding to the peaks in the mass spectral scan shown in FIG. 7.

The discrepancy between the in-solution and on-chip results can be explained in view of the mechanism of action of PNGase F and the efficient, on-line nature of the chip. According to Rasmussen et al., 1992 (see FIG. 8), PNGase F acts by first cleaving the C—N bond of the glycosylated asparagine side chain, and the asparagine residue is converted to aspartic acid. The cleaved glycan is an amino glycan initially, but the amino group is slowly hydrolyzed to a hydroxyl group with the release of ammonia. Taking into account the masses of each peak in FIG. 7, we postulated that peak 310 corresponds to amino glycan of G0, which is hydrolyzed to hydroxyl glycans (peaks 313 and 315) upon a long incubation. To test this hypothesis, a time-course experiment was conducted in which the sample was allowed to stay in the deglycosylation column in our chip for 0, 15, 30, 60, 120 and 240 minutes, respectively. Indeed, peak 310 decreased and peaks 313 and 315 increased in intensity with each prolonged incubation time. Similarly, the peaks for G1 in the in-solution analysis (304 and 306) also decreased over time, and 311 increased. Thus, based on the time-dependent changes and masses of the peaks, we conclude (see FIG. 9) that peaks 310, 311 and 312 correspond to amino glycans, and peaks 313-316 correspond to hydroxyl glycans. There are two peaks (313 and 315, and 314 and 316) for each hydroxyl glycan, because hydroxyl glycans isomerize easily between the α-anomer and the β-anomer.

The on-line nature of the chip also contributes to efficiency of the reaction. When a sample enters the deglycosylation column and moves along, each "front" of the sample comes in contact with an excess amount of the enzyme and is cleaved instantly. On the other hand, the in-solution incubation mixture contains a lower enzyme to substrate ratio for each substrate, and the reaction tends to leave a population of various incompletely digested products. Furthermore, in the on-line process, the cleaved glycans continue to move along, bind to the trapping column, and become separated in the separation column. Thus, the glycans are bound by other molecules most of the time and have less chance to isomerize or undergo other chemical reactions.

Figure 10:
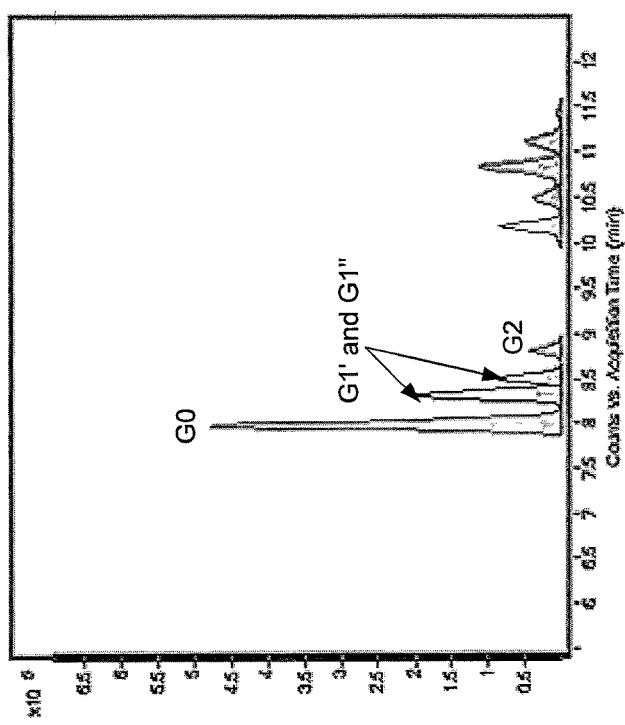
FIG. 10 demonstrates separation of glycan isoforms G1' and G1" after a short gradient in liquid chromatography.

The ability of the present invention to catch the amino glycans makes it possible to separate the two isoforms of G1 efficiently. G1 exists as two isomers (G1' and G1" in FIG. 11). It was believed that G1' and G1" could only be separated using a very long gradient. Therefore, it has been a problem to accurately analyze glycan compositions without spending the resources and time for a long separation step. We discovered, however, that the amino forms can be readily separated. The following short gradient was used to run the separation column in the chip described in this example, and G1' and G1" were clearly resolved (FIG. 10) in a matter of minutes:

| Time (min) | % Solvent B |
| --- | --- |
| 0 | 2 |
| 10 | 22 |
| 12 | 80 |

| Time (min) | % Solvent B |
| --- | --- |
| 15 | 80 |
| 16 | 2 |

Thus, these results demonstrate that the chips described in this disclosure not only significantly shorten the time required for glycan analysis, but the data obtained from the chips reflect the structures of the glycans more faithfully. In addition, only a small amount of initial sample is required for the chip to achieve the same results. The sample in this example contained only 100 ng of glycoproteins, and the signals in mass spectra were very high. Therefore, a lower amount of sample can be used.

Exemplary Embodiments

Embodiments of the present invention include, without being limited to, the following:

A. A microfluidic device for removing carbohydrate from a glycoprotein, comprising:
a deglycosylation column comprising a solid support and an enzyme immobilized to the solid support, wherein the enzyme is capable of cleaving carbohydrates from glycoproteins;
a trapping column that is capable of binding carbohydrates;
a separation column capable of separating carbohydrates; and
a plurality of inlet/outlet ports;
wherein said ports are configured so that when said device is coupled with a switching element that comprises at least one channel, the combination of said ports, columns and at least one channel forms a valve system that can be switched between at least a first state and a second state, the first state allowing fluid communication between the deglycosylation column and the trapping column, and the second state allowing fluid communication between the trapping column and the separation column.

B. The device of embodiment A, further comprising a cleaning column capable of binding proteins, wherein the cleaning column is configured to be connectable to the deglycosylation column and/or the trapping column by the valve system.

C. The device of embodiment A or B, wherein the enzyme is N-glycosidase F.

D. The device of any one of embodiments A-C, wherein the solid support in the deglycosylation column comprises beads or a monolithic medium.

E. The device of any one of embodiments A-D, wherein the separation column is a liquid chromatography column.

F. The device of any one of embodiments A-D, wherein the separation column is a capillary electrophoresis apparatus.

G. The device of any one of embodiments A-F that comprises two layers, wherein the deglycosylation column is in one layer, and the trapping column and separation column are in the other layer.

H. The device of any one of embodiments B-F that comprises three layers, wherein the deglycosylation column is in a first layer, the cleaning column is in a second layer, and the trapping column and separation column are in a third layer.

I. A system for analyzing a sample, comprising the device of any one of embodiments A-H, the switching element, and a mass spectrometer.

J. The system of embodiment I, wherein the mass spectrometer comprises an electrospray ion source.

K. A method for analyzing the carbohydrate moieties of glycoproteins, comprising:
applying a sample that may comprise glycoproteins to the device of embodiment A;
digesting the glycoproteins in the deglycosylation column to result in cleaved carbohydrates;
binding the cleaved carbohydrates to the trapping column;
eluting the cleaved carbohydrates from the trapping column; and
separating the cleaved carbohydrates with the separation column.

L. The method of embodiment K, further comprising removing proteins after the digesting with a cleaning column capable of binding proteins.

M. The method of embodiment K or L, wherein the cleaved carbohydrates are separated by liquid chromatography.

N. The method of embodiment K or L, wherein the cleaved carbohydrates are separated by capillary electrophoresis.

O. The method of any one of embodiments K-N, further comprising analyzing the cleaved carbohydrates using mass spectrometry.

P. The method of any one of embodiments K-O, wherein the sample contains up to 50 ng of glycoproteins.

Q. The method of any one of embodiments K-P, wherein the method is completed within 10 minutes.

R. The method of any one of embodiments K-Q that is performed under conditions that allow at least some of the cleaved carbohydrates to remain in amino glycan forms. Preferably, a substantial amount of the cleaved carbohydrates remain in amino glycan forms.

S. The method of any one of embodiments K-R, wherein the glycoproteins are digested with N-glycosidase F.

T. A kit for glycan analysis, comprising the device of any one of embodiments A-H and at least one reagent for sample dilution or column elution.

REFERENCES

Palm and Novotny (2005), "A monolithic PNGase F enzyme microreactor enabling glycan mass mapping of glycoproteins by mass spectrometry," Rapid Comm. Mass Spectrometry 19: 1730-1738.

Rasmussen et al. (1992), "Identification and derivatization of (oligosaccharyl)amines obtained by treatment of asparagine-linked glycopeptides with N-GLYCANASE enzyme," J. Am. Chem. Soc., 114(3): 1124-1126.

Becker et al. (1986), "Fabrication of Microstructures with High Aspect Ratios and Great Structural Heights by Synchrotron Radiation Lithography Galvanoforming, and Plastic Moulding (LIGA Process)," Microelectronic Engineering 4(1):35-36.

Ehrfeld et al. (1988), "1988 LIGA Process: Sensor Construction Techniques via X-Ray Lithography," Tech. Digest from IEEE Solid-State Sensor and Actuator Workshop, Hilton Head, S.C.

Guckel et al. (1991), J. Micromech. Microeng. 1: 135-138.

Znotins et al. (1987), Laser Focus Electro Optics, at pp. 54-70.

U.S. Pat. Nos. 6,702,256; 5,291,226 and 5,305,015.

U.S. Patent Publication No. 2006/0171855.

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

A number of embodiments of the invention have been described. Nevertheless, it will be understood that various modifications may be made without departing from the spirit and scope of the invention.

What is claimed is:

1. A method for analyzing the carbohydrate moieties of glycoproteins, comprising:
    applying a sample comprising glycoproteins to a deglycosylation column, wherein the glycoproteins in the deglycosylation column are digested to result in cleaved carbohydrates and at least some of the cleaved carbohydrates remain in amino glycan forms;
    without precipitating the cleaved carbohydrates, binding the cleaved carbohydrates to a trapping column;
    eluting the cleaved carbohydrates from the trapping column; and
    separating amino glycan forms of the cleaved carbohydrates from hydroxyl for of the cleaved carbohydrates using a separation column to resolve the cleaved carbohydrates, wherein the separating of the cleaved carbohydrates comprises separating isomers of the cleaved carbohydrates; and
    separately analyzing the resolved cleaved carbohydrates.

2. The method of claim 1, further comprising removing proteins after the digesting with a cleaning column capable of binding proteins.

3. The method of claim 1, wherein the cleaved carbohydrates are separated from one another by liquid chromatography.

4. The method of claim 1, wherein the cleaved carbohydrates are separated from one another by capillary electrophoresis.

5. The method of claim 1, wherein the resolved cleaved carbohydrates are analyzed using mass spectrometry.

6. The method of claim 1, wherein the sample contains up to 50 ng of glycoproteins.

7. The method of claim 1, wherein the glycoproteins are digested with N-glycosidase F.

8. The method of claim 1, wherein the sample is applied to a microfluidic device comprising:
    the deglycosylation column;
    the trapping column;
    the separation column;
    a plurality of inlet/outlet ports; and
    a switching element comprising at least one channel;
    the method further comprising: switching the microfluidic device between a first state that allows fluid communication between the deglycosylation column and the trapping column and a second state that allows fluid communication between the trapping column and the separation column.

9. The method of claim 8, wherein the microfluidic device further comprises a cleaning column capable of binding proteins, and wherein the method further comprises applying the sample to the cleaning column after the digesting.

10. The method of claim 8, wherein the microfluidic device comprises two layers, wherein the deglycosylation column is in one layer, and the trapping column and separation column are in the other layer.

11. The method of claim 8, wherein the microfluidic device comprises three layers, wherein the deglycosylation column is in a first layer, the cleaning column is in a second layer, and the trapping column and separation column are in a third layer.

12. The method of claim 1, wherein at least 30% of the cleaved carbohydrates remain in amino glycan forms.

13. The method of claim 1, wherein the process of
    applying a sample to a deglycosylation column,
    binding the cleaved carbohydrates,
    eluting the cleaved carbohydrates, and
    separating the cleaved carbohydrates
is achieved in one minute to an hour.

14. The method of claim 1, wherein the separating of the cleaved carbohydrates comprises separating isomers of an amino glycan form of at least one of the cleaved carbohydrates.

15. The method of claim 1, wherein the separating of the cleaved carbohydrates comprises separating isomers of G1 in amino glycan form.

16. The method of claim 1, wherein at least 30% of the cleaved carbohydrates remain in amino glycan forms.

17. A method for separating the carbohydrate moieties of glycoproteins, comprising:
    obtaining a microfluidic device comprising:
        a deglycosylation column comprising a solid support and an enzyme immobilized to the solid support, wherein the enzyme is capable of cleaving carbohydrates from glycoproteins;
        a trapping column that is capable of binding carbohydrates;
        a separation column capable of separating carbohydrates;
        a plurality of inlet/outlet ports; and
        a switching element comprising at least one channel;
    applying a sample that may comprise glycoproteins to the deglycosylation column to result in cleaved carbohydrates, wherein at least some of the cleaved carbohydrates remain in amino glycan forms;
    switching the device to a first state that allows fluid communication between the deglycosylation column and the trapping column to bind the cleaved carbohydrates to the trapping column, without precipitating the cleaved carbohydrates;
    switching the device to a second state that allows fluid communication between the trapping column and the separation column to elute the cleaved carbohydrates to the separating column; and
    separating amino glycan forms of the cleaved carbohydrates from hydroxyl forms of the cleaved carbohydrates using the separation column to resolve the cleaved carbohydrates.

* * * * *

UNITED STATES PATENT AND TRADEMARK OFFICE
CERTIFICATE OF CORRECTION

PATENT NO. : 10,209,259 B2
APPLICATION NO. : 14/664709
DATED : February 19, 2019
INVENTOR(S) : Magdalena Anna Ostrowski et al.

It is certified that error appears in the above-identified patent and that said Letters Patent is hereby corrected as shown below:

In the Claims

Column 13, Line 20, Claim 1, delete "for" and insert -- forms --, therefor.

Signed and Sealed this
Twenty-second Day of October, 2019

Andrei Iancu
*Director of the United States Patent and Trademark Office*